United States Patent
Luxton et al.

(10) Patent No.: US 9,610,584 B2
(45) Date of Patent: Apr. 4, 2017

(54) PARTICLE FACILITATED TESTING

(75) Inventors: Richard William Luxton, Bristol (GB); Janice Helen Kiely, Bristol (GB); Patrick Wraith, Bristol (GB)

(73) Assignee: UNIVERSITY OF THE WEST OF ENGLAND, BRISTOL, Bristol (GB)

( * ) Notice: Subject to any disclaimer, the term of this patent is extended or adjusted under 35 U.S.C. 154(b) by 559 days.

(21) Appl. No.: 12/532,072

(22) PCT Filed: Mar. 25, 2008

(86) PCT No.: PCT/GB2008/000993
§ 371 (c)(1),
(2), (4) Date: Dec. 22, 2009

(87) PCT Pub. No.: WO2008/114025
PCT Pub. Date: Sep. 25, 2008

(65) Prior Publication Data
US 2010/0248345 A1   Sep. 30, 2010

(30) Foreign Application Priority Data

Mar. 21, 2007 (GB) .................................. 0705428.1
Apr. 18, 2007 (GB) .................................. 0707480.0

(51) Int. Cl.
C12M 1/33 (2006.01)
C12M 1/34 (2006.01)
(Continued)

(52) U.S. Cl.
CPC ............. B01L 99/00 (2013.01); C12M 47/06 (2013.01); G01N 33/54326 (2013.01)

(58) Field of Classification Search
CPC .. B01L 99/00; B01L 3/502738; B01L 3/5027; B01L 2300/049; B01L 2400/0633;
(Continued)

(56) References Cited

U.S. PATENT DOCUMENTS 7,105,357 B1* 9/2006 Kalkum et al. ............... 436/180
2001/0050555 A1* 12/2001 Hawkins et al. .............. 324/204
(Continued)

FOREIGN PATENT DOCUMENTS

EP  1 146 347  7/2005
EP  1 650 297  4/2006
(Continued)

OTHER PUBLICATIONS

Kiely, et al. "Paramagnetic particle detection for use with an immunoassay based biosensor," pp. 270-275, *IET Sci. Meas. Technol.*, vol. 1, No. 5, Sep. 2007.

Luxton, et al. "Use of External Magnetic Fields to Reduce Reaction Times in an Immunoassay Using Micrometer-Sized Paramagnetic Particles as Labels (Mangetoimmunoassay)," pp. 1715-1719, *Analytical Chemistry*, vol. 76, No. 6, Mar. 15, 2004.

(Continued)

*Primary Examiner* — William H Beisner
*Assistant Examiner* — Danielle Henkel
(74) *Attorney, Agent, or Firm* — Marshall, Gerstein & Borun LLP

(57) ABSTRACT

Magnetic particles are distributed across a fluid flow by applied magnetic field to interact with a test substance in fluid. Alternatively or additionally, particles, which may be magnetic, are combined with cells and energy, e.g. ultrasonic energy, is applied to cause the particles to create a lysate. Alternatively or additionally, the size of a quantity of magnetic particles is assessed by its impact on the tuning mechanism of a controlled oscillator that is affected by the particles.

17 Claims, 14 Drawing Sheets

(51) Int. Cl.
  *G01N 33/53*   (2006.01)
  *B01L 99/00*   (2010.01)
  *C12M 1/00*    (2006.01)
  *G01N 33/543*  (2006.01)

(58) Field of Classification Search
  CPC ........ G01N 33/54326; G01N 27/745; G01N 2035/00247; G01N 2035/00574; G01N 35/0098; C12M 47/06; B01J 19/0046; B01J 2219/0034; B01J 2219/00439; B01J 2219/00459; B01J 2219/005; B01J 2219/00585; B01J 2219/00596; B01J 2219/00605; B01J 2219/00612; B01J 2219/00648; B01J 2219/00659; B01J 2219/00722; B01J 2219/00317; G06F 7/723; G11C 7/1066; Y10T 436/25; C40B 40/06; C40B 60/14
  USPC .............. 435/287.1, 306.1; 422/69
  See application file for complete search history.

(56) References Cited

U.S. PATENT DOCUMENTS

2005/0013741 A1* 1/2005 a'Brassard .............. B03C 1/288
                                                    210/695
2007/0116600 A1* 5/2007 Kochar et al. ................. 422/65
2008/0309329 A1* 12/2008 Kahlman et al. ............. 324/228

FOREIGN PATENT DOCUMENTS

| WO | WO 03/031977    | 4/2003  |
| WO | WO 2005/111614  | 11/2005 |
| WO | WO 2005/111615  | 11/2005 |
| WO | WO 2006/015326  | 2/2006  |

OTHER PUBLICATIONS

International Search Report for International Application No. PCT/GB2008/000993 dated Jun. 30, 2008.

* cited by examiner

PARTICLE FACILITATED TESTING

1. FIELD

The invention relates to apparatus for, and methods of, testing fluid, and to apparatus for and methods of lysing cells using particles.

2. BACKGROUND

It is known to utilise magnetic particles to capture an analyte in a solution under test. Conventionally, the magnetic particles are coated with a substance to which the analyte will attach. A sensor surface in contact with the solution is provided with a similar coating and a magnetic field is applied to urge the magnetic particles onto the surface. Analyte bound to the magnetic particles then becomes attached to the sensor surface also. Thus, magnetic particles that have picked up analyte become immobilised on the sensor surface. An inductor located near to the sensor surface is used to quantify the number of magnetic particles that are so immobilised. The inductor forms part of a resonant electrical circuit. The resonant frequency of this circuit is determined in part by the inductance of this inductor and the inductance of the inductor is determined in part by the quantity of immobilised magnetic particles.

In the investigation of cell organelles and measurement of intracellular proteins, cells need to be disrupted or lysed, releasing the intracellular components for study. Freeze-thaw methods are commonly used to lyse both bacterial and mammalian cells. These methods involve freezing a cell suspension using a dry ice/ethanol bath or freezer and then thawing the material at room temperature or 37° C. This method of lysis causes cells to swell and ultimately break as ice crystals form during the freezing process and then contract during thawing. Multiple cycles are necessary for effective lysis, and the process can be time consuming. However, the freeze/thaw methods have been shown to release proteins located in the cytoplasm of bacteria effectively, and are recommended for the lysis of mammalian cells in some protocols.

Another approach commonly used to disrupt cells is to solubilise the cell membrane using a detergent. This has the added advantage of releasing membrane bound proteins but may dissociate protein complexes. Classically, physical methods have been used to disrupt cells, such as grinding tissue in a pestle and mortar or using a blade either as a scalpel or a liquidiser. There are some inherent disadvantages to mechanical lysis methods such as localized heating within a sample leading to protein denaturation and aggregation.

Ultrasound has also been used as a method of physical cell disruption which is based on the generation of high frequency pulses of pressure. Sonication (i.e. the process of disrupting the cell using sound waves) generates heat which may denature proteins, so the process should be performed in an ice bath. Some studies have shown that lysis using detergents to solubilise the cell membranes is more efficient at releasing intracellular protein than ultrasound.

3. BRIEF SUMMARY

According to one aspect, the invention provides apparatus for testing a fluid, the apparatus comprising magnetic particles, a flow path for fluid and means for exerting magnetic force on the particles to distribute them across part of the flow path such that a test substance flowing along the path and through the distribution can alter the particles. The invention also consists in a method of testing fluid, the method comprising exerting magnetic force on magnetic particles to distribute them across part of a flow path such that a test substance in a fluid flowing along the path and through the distribution can alter the particles.

The magnetic particles can be made from, for example, ferromagnetic, diamagnetic, paramagnetic or super-paramagnetic material.

In certain embodiments, the magnetic particles can be thought of as being formed into a sieve or net or the like by the action of the magnetic field. In certain embodiments, the magnetic field forms the magnetic particles into strands or fronds or the like.

In certain embodiments, the magnetic particles are altered by the test substance in as much as the test substance binds to the particles. The particles may be provided with a coating to facilitate such binding. For example, where the test substance is an antigen, the magnetic particles can be coated with an antibody to which the antigen will bind. As a further example, the test substance could be a chemical compound and the coating could be another compound which will bind with the first. It will be apparent that suitable coatings will be available to capture other types of test substance.

In certain embodiments, magnetic force can be applied to move the magnetic particles to an examination site. The examination site may contain means for capturing magnetic particles that have been altered by the test substance. Taking again the example where the magnetic particles are altered by the attachment of the test substance, the capture means may include a surface to which magnetic particles bearing test substance become attached.

In certain embodiments of the invention, the magnetic particles are manipulated by varying a magnetic field that is applied to the particles. This variation can be achieved by, for example, repositioning one or more permanent magnets that contribute towards the field or by adjusting the energisation of one or more electromagnets that contribute towards the field.

In certain embodiments, sensing means is provided for assessing the quantity of magnetic particles that reside in an examination space. For example, the sensing means may utilise a magneto-resistive sensor, a micro-machined cantilever device or a superconducting quantum interference device in order to detect the particles' magnetism.

The fluid under test could be gaseous, in which case the fluid could be, for example, air and the test substance could be, for example, a pollutant. Alternatively, the fluid could be liquid, in which case the fluid could be, for example, drinking water and the test substance could be, for example, a bacterium.

According to another aspect, the invention provides a cell adapted to fit, in a removable fashion, into apparatus for testing for a substance in a fluid, the cell comprising a container holding magnetic particles that are alterable by the substance and means for permitting fluid that might contain the substance to pass through the container.

In certain embodiments, such a cell might include sensing means with which the particles can interact, with the interaction of a given particle with the sensing means being dependent on the alteration of that particle by the test substance. In certain embodiments, the sensing means may comprise a surface to which the particles can attach, the surface being such that the ability of a given particle to attach depends on the alteration of that particle by the test substance.

In certain embodiments, the cell may include assessing means whose electrical properties are alterable by proximity of magnetic particles. For example, the assessing means could be a magnetoresistive sensor or an inductor.

According to another aspect, there is provided apparatus for lysing a cell, the apparatus comprising a chamber for holding the cell to be lysed and means for introducing energy into the chamber, wherein the chamber contains a plurality of particles which may be excited by the energy to enhance lysing of the cell.

The means for introducing energy into the chamber may comprise means for introducing sound waves into the chamber.

The means for introducing sound waves into the chamber may comprises a sonicator probe.

Additionally or alternatively, the means for introducing sound waves into the chamber may comprise an ultrasonic transducer.

The means for introducing energy into the chamber may be operable to introduce energy into the chamber in a pulsed manner.

The particles may be of a plastics material.

Alternatively, the particles may be of metal.

Alternatively, the particles may be of a combination of metal and a plastics material.

The plurality of particles may be provided with a binding agent to which components of a lysed cell may bind.

The chamber may comprise a sensor surface provided with a binding agent to which components of a lysed cell may bind.

A label may be provided to identify a complex formed when a component binds to the binding agent.

The label may comprise an enzyme.

The plurality of particles are preferably in the range from approximately 0.1 µm to approximately 100 µm in diameter.

The plurality of particles are more preferably in the range from approximately 1 µm to approximately 20 µm in diameter.

In certain embodiments, the plurality of particles may be magnetic.

For example, the plurality of particles may be of a paramagnetic, ferromagnetic, diamagnetic or super-paramagnetic material.

The apparatus may further comprise sensing means for sensing the magnetic particles.

The apparatus may further comprise means for generating a magnetic field to draw the magnetic particles towards the sensing surface of the chamber.

The means for generating a magnetic field may comprise a permanent magnet.

Additionally or alternatively, the means for generating a magnetic field may comprise an electromagnet.

According to a further aspect of the invention, there is provided a method of lysing a cell, the method comprising introducing the cell into a chamber containing a plurality of particles and introducing energy into the chamber to excite the plurality of particles.

The energy introduced into the chamber may comprise sound waves.

The sound waves may be introduced into the chamber using a sonicator probe.

Additionally or alternatively the sound waves may be introduced into the chamber using an ultrasonic transducer.

The energy may be introduced into the chamber in a pulsed manner.

The particles may be of a plastics material.

Alternatively the particles may be of metal.

Alternatively, the particles may be of a combination of metal and a plastics material.

The plurality of particles may be provided with a binding agent to which components of a lysed cell may bind.

The chamber may comprise a sensor surface provided with a binding agent to which components of a lysed cell may bind.

A label may be provided to identify a complex formed when a component binds to the binding agent.

The label may comprise an enzyme.

The plurality of particles are preferably in the range from approximately 0.1 µm to approximately 100 µm in diameter.

The plurality of particles are more preferably in the range from approximately 1 µm to approximately 20 µm in diameter.

In certain embodiments, the plurality of particles may be magnetic.

For example, the plurality of particles may be of a paramagnetic, ferromagnetic, diamagnetic or super-paramagnetic material. Sensing means may be used to sense the magnetic particles.

A magnetic field may be generated to draw the magnetic particles towards the sensor surface of the chamber.

The magnetic field may be generated using means comprising a permanent magnet.

Additionally or alternatively, the magnetic field may be generated using means comprising an electromagnet.

According to yet another aspect, the invention provides fluid testing apparatus comprising a binding site to which can attach magnetic particles which have become associated with a target substance in the fluid, an oscillator circuit comprising inductance and capacitance in resonant combination to set the frequency of the circuit's output signal and adjustment means for altering the capacitance, wherein the inductance is influenced by the quantity of magnetic particles at the binding site and the adjustment means is arranged to alter the capacitance to maintain said frequency in the face of changes in said quantity.

4. BRIEF DESCRIPTION OF THE DRAWINGS

By way of example only, certain embodiments of the invention will now be described with reference to the accompanying drawings, in which:

FIG. 1 provides an overview of a fluid analysis system;

5. DETAILED DESCRIPTION

5.1 Analyte Detection

Figure 1:
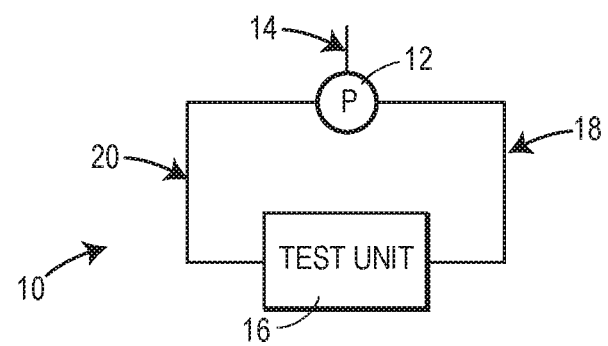

FIG. 1 shows an overview of a fluid analysis system 10. A pump 12 is provided with an inlet 14 for acquiring a sample of liquid that is to be examined by a test unit 16. After a sample of liquid has been acquired through inlet 14, the pump then operates to repeatedly circulate the liquid sample through the test unit 16 via tubes 18 and 20. The pump 12 pumps the liquid to the test unit 16 through tube 18 and the liquid returns from the test unit 16 to the pump 12 through tube 20. The test unit 16 is configured to detect the presence of a particular antigen in the liquid that is being pumped through the test unit 16. Henceforth, this antigen shall be referred to as the target antigen.

Figure 2:
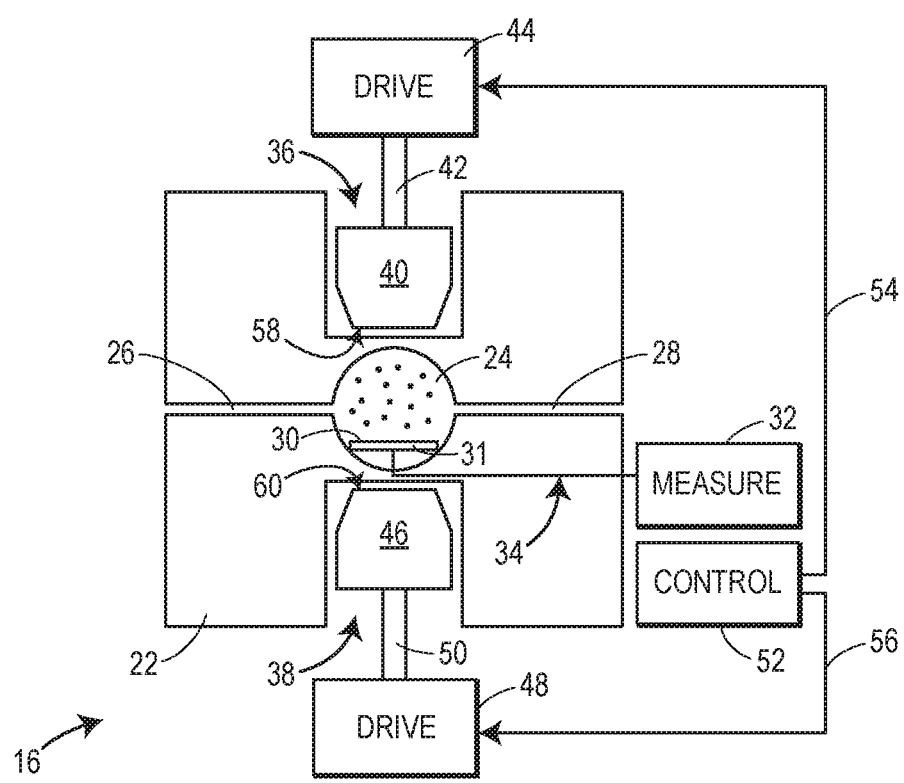
FIG. 2 shows in more detail the test unit of the system shown in FIG. 1.

The test unit 16 is shown in more detail in FIG. 2. The main structure of the test unit 16 is provided by a block 22 of plastics material. A spherical measurement chamber 24 is formed in the centre of the block 22. Two bores 26 and 28 are formed in the block 22 to connect the measurement chamber 24 with the exterior of the block. The mouth that bore 28 presents to the exterior of the block 22 is connected to tube 18 and the mouth that bore 26 presents to the exterior of the block 22 is connected to tube 20. In this way, the pump 12 can pass the test liquid through the measurement chamber 24. The measurement chamber 24 is populated with particles of paramagnetic material, which are denoted in FIG. 2 by the black dots lying within the measurement chamber 24. The paramagnetic particles are treated with a coating of a particular antibody to which the target antigen will bind.

The measurement chamber 24 is preferably shaped so as to reduce the speed of the test liquid as it flows through the measurement chamber 24, to reduce disturbance to the paramagnetic particles, which will usually be manipulated to form specific configurations, as will be described below.

A square plate 31 is mounted in the bottom of the measurement chamber 24. The plate 31 has upper and lower major surfaces facing towards and away from the centre of the measurement chamber, respectively. The upper major surface of the plate 31 is covered with a coating 30 of the same antibody that has been applied to the paramagnetic particles. The lower major surface of the plate 31 is provided with an electrical coil which is connected to a measurement unit 32 by means of electrical connection 34.

Two cavities 36 and 38 are provided in the upper and lower surfaces of the block 22. A permanent magnet 40 is slidably mounted within cavity 36. A shaft 42 connects magnet 40 to a drive unit 44. The drive unit 44 is configured to act on the shaft 42 to vary the position of magnet 40 within cavity 36. That is to say, the drive unit can raise and lower the magnet 40 in the cavity 36 so as to vary the distance of the magnet 40 from the measurement chamber 24. Analogously, a permanent magnet 46 is slidably mounted in cavity 38 and can be moved by drive unit 48 by means of rod 50. The positions of the magnets 40 and 46 within the cavities 36 and 38 are governed by a control unit 52 that applies control signals to the drive units 44 and 48 through connections 54 and 56. Surface 58 constitutes the north pole of magnet 40 and surface 60 constitutes the south pole of magnet 46. The magnets 40 and 46 are closely fitted to their corresponding cavities 36 and 38 so that the pole faces 58 and 60 and the major surfaces of the plate 31 remain parallel with one another as the magnets are moved.

The positions of the magnets 40 and 46 relative to the centre of the measurement chamber 24 dictate the magnetic field that is experienced by the paramagnetic particles that are located within the measurement chamber. In order to promote the capture of any target antigen that is present within the test liquid that is flowing through the measurement chamber 24, the magnets 40 and 46 are positioned so as to generate within the measurement chamber 24 a magnetic field that causes the paramagnetic particles to distribute themselves across the measurement chamber in the manner of a sieve acting on the test liquid that is flowing through the measurement chamber 24. In this configuration, the paramagnetic particles form strands that extend across the flow within the measurement chamber 24 and generally attempt to extend between the pole faces 58 and 60, following the lines of magnetic force extending between the pole faces 58 and 60. These strands are illustrated schematically in FIG. 3 which shows the central portion of the block 22, focussing on the measurement chamber 24.

Figure 3:
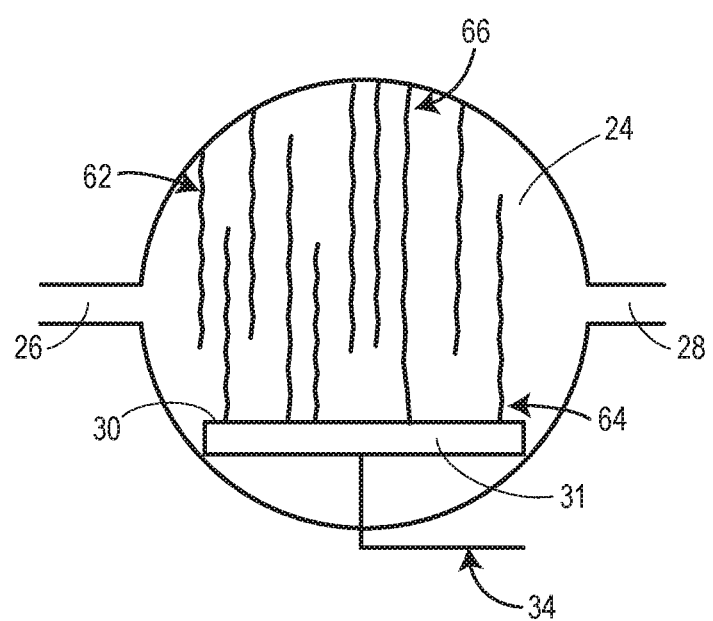
FIG. 3 illustrates the distribution of magnetic particles within the measurement chamber of the test unit of FIG. 2 under certain magnetic field conditions.

In FIG. 3, the strands are denoted by irregular vertical lines within the measurement chamber 24. Some strands, e.g. 62, may form extending from the upper surface of the measurement chamber. Other strands, e.g. 64, form extending from the base of the measurement chamber, which is effectively provided by the plate 31. Yet other strands, e.g. 66, may extend entirely between the base and upper surface of the measurement chamber 24. In this condition, the paramagnetic particles are distributed across the flow of the test liquid through the measurement chamber 24 which facilitates the paramagnetic particles' capture, via their antibody coating, of target antigen in the test liquid. Accordingly, the state of the magnetic field required to place the paramagnetic particles in this condition shall be referred to as the "capture state". The precise positions of the magnets 40 and 46 that are required to transform the magnetic field in the measurement chamber 24 into the capture state will depend upon various parameters of the precise design of the equipment and can be determined through experimentation. Examples of such parameters include the material and size of the paramagnetic particles, the material and size of the magnets 40 and 46 and the diameter of the measurement chamber 24.

The magnetic field within the measurement chamber 24 can also be adjusted to a so-called "collection state" in which the paramagnetic particles are drawn down to collect over the upper major surface of the plate 31. The collection state of the magnetic field can be achieved by moving the magnets 40 and 46 to their maximum and minimum distances, respectively, from the centre of the measurement chamber 24. When the magnetic field in the measurement chamber 24 is in the collection state, the paramagnetic particles are urged onto the antibody coating 30 on the plate 31. Some of the paramagnetic particles in contact with the coating 30 will have target antigen bound onto them. These particles can then become linked to the coating 30 by the target antigen that they carry and therefore become immobilised on the plate 31.

In order to examine the test liquid for the presence of the target antigen, the magnets 40 and 46 are moved to cycle the magnetic field in the measurement chamber 24 between the capture and collection states. When desired, the quantity of paramagnetic particles that have become attached to the antibody coating 30 on the plate 31 can be assessed electronically, as will now be explained.

5.2 Sensing Arrangement

Figure 4:
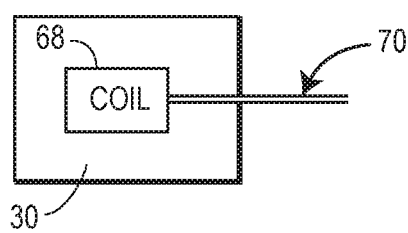
FIG. 4 illustrates schematically the underside of the plate that is disposed at the bottom of the measurement chamber that is shown in FIG. 2.

FIG. 4 shows the lower major surface of the plate 31. An electrical coil 68 is provided on the lower major surface of the plate 31. A pair of supply conductors 70 extend from the coil and provide the connection 34 to the measurement unit 32. The coil 68 forms part of a voltage controlled oscillator (VCO), the remainder of which is housed within the measurement unit 32.

Figure 5:
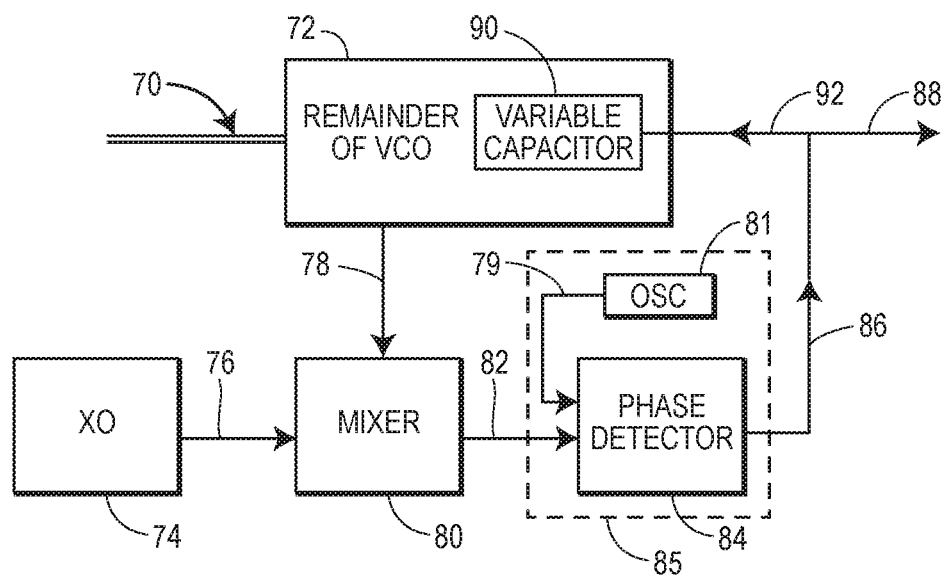
FIG. 5 illustrates schematically the main elements of the measurement unit of the test unit that is shown in FIG. 2.

In FIG. 5, the circuitry that supplements coil 68 to form the VCO is indicated 72. From another perspective, coil 68 is simply an inductor that forms part of a VCO design and which has been located remote from the other components of the design. It should be noted, however, that the coil 68 and the measurement unit are, preferably, physically close to the measurement chamber 24. VCO designs that are suitable for adaptation in this manner are known to the skilled person. The VCO incorporates a variable capacitor 90, which is, for example, a variable capacitance diode. Together, the coil 68 and the capacitor 90 determine the frequency of the VCO's output signal.

The measurement unit 32 also includes a crystal oscillator 74. The crystal oscillator 74 produces a 70 MHz output signal on line 76. The voltage controlled oscillator produces a signal on line 78 whose frequency the measurement unit 32 endeavours to maintain locked to a frequency of 70 KHz away from the output signal of the crystal oscillator 74. To achieve this end, output signals of the VCO and the crystal oscillator 74 are mixed together in a mixer 80 and resulting signal is provided on line 82 as one input to a phase detector 84. The other input to the phase detector 84 is provided over line 79 and is the output signal of a variable oscillator 81. The variable oscillator 81 and the phase detector 84 are integrated into a single package 85, which may also contain the other elements of the system of FIG. 5, with the exception of the crystal oscillator 74. The variable oscillator 81 is tuned so that the output signal that it provides on line 79 has a frequency of 70 KHz. The phase detector 84 produces a DC voltage on line 86 that is proportional to the phase difference between its two input signals. This DC voltage is sensed on line 88 (and is referred to henceforth as a detection signal) and is also applied via line 92 to the variable capacitor 90 within the VCO. This voltage controls the capacitance of the variable capacitor 90, thereby tuning the frequency of the VCO's output. It will be apparent to the skilled person that the elements shown in FIG. 5 are formed into a phase locked loop (PLL), or more accurately a frequency locked loop (FLL) for the purpose of locking the frequency of the output signal of the mixer 80 to 70 KHz, i.e. to the frequency of the output of the variable oscillator 81. This means that the PLL acts to maintain the output signal of the VCO at 69.93 MHz.

As mentioned earlier, coil 68 forms part of the voltage controlled oscillator that is the object of the PLL. The frequency of the output of the VCO that is supplied over line 78 is governed in part by the inductance of coil 68. In turn, the inductance of coil 68 is governed by the distribution of the paramagnetic particles within the measurement chamber 24 and in particular by the immobilisation of target antigen carrying paramagnetic particles on the coating 30. Accordingly, the voltage of the output of the phase detector 84 that is sensed on line 88 contains information about the behaviour of the paramagnetic particles and, in turn, about test antigen in the measurement chamber 24. In order to make deductions about test antigen in the measurement chamber 24, the voltage of the output of the phase detector 84 is recorded over time as the magnetic field within the measurement chamber 24 is varied. A typical assay will now be described.

5.3 Results

Figure 6:
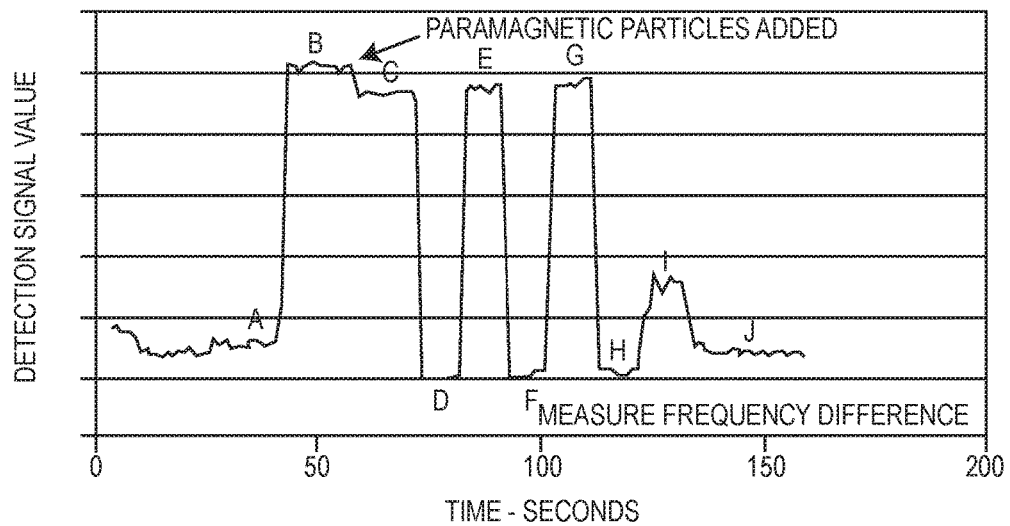
FIG. 6 illustrates the type of response that can be obtained from the measurement unit of FIG. 5 during an assay.

FIG. 6 shows a plot of a sandwich assay performed using apparatus according to the present embodiment of the invention. FIG. 6 plots the detection signal versus time. At the beginning of the measurement process, the measurement chamber 24 contains just a buffer solution and the detection signal value is A. Then, the magnets 40 and 46 are positioned so as to bring the magnetic field in the measurement chamber 24 into the collection state, which causes the detection signal value to change to B. Next, a quantity of liquid containing antibody coated paramagnetic particles mixed with target antigen is added to the buffer solution in the measurement chamber 24. This causes a marked drop in the detection signal value to C. At this point, the paramagnetic particles are clumped on the upper surface of the plate 31. The magnets 40 and 46 are then repositioned to change the magnetic field within the measurement chamber 24 to the capture state. This reduces the detection signal value to D. After 30 seconds, the magnets 40 and 46 are repositioned to change the magnetic field to the collection state, whereupon the detection signal value changes to E. After 30 seconds, the magnets 40 and 46 are repositioned to change the magnetic field back to the capture state such that the detection signal value changes to F. After 30 seconds, the magnets 40 and 46 are repositioned to change the magnetic field to the collection state, whereupon the detection signal value changes to G. After a further 30 seconds, the magnets 40 and 46 are drawn back as far as possible from the measurement chamber 24 and the detection signal value changes to H and the paramagnetic particles are allowed to relax on the upper surface of the plate 31 for 30 seconds. Then, magnet 40 is driven to its point of closest approach to the chamber 24 whilst magnetic 46 is kept remote from the chamber 24. This causes the detection signal value to change to I. During this time, the proximity of magnet 40 causes any paramagnetic particles that are not bound to the coating on plate 31 to move away from the plate. Then, after 30 seconds, magnet 40 is retracted as far as possible from the sample chamber 24 such that the detection signal value changes to J.

In an alternative method, the paramagnetic particles are added to the buffer solution in the measurement chamber 24 before the magnets 40 and 46 are positioned so as to bring the magnetic field in the measurement chamber 24. In this method, the magnets 40 and 46 are positioned so as to cause the magnetic field to be in the capture state, causing the detection signal value to change to D immediately.

Various metrics can be derived from the time varying detection signal value shown in FIG. 6. For example, the following metrics could be used:

J–H
J–A
(J–H)/A
(J–H)/B
(J–H)/(B–C)

The time varying detection signal value is typically normalised and smoothed prior to calculating the metrics.

Figure 7:
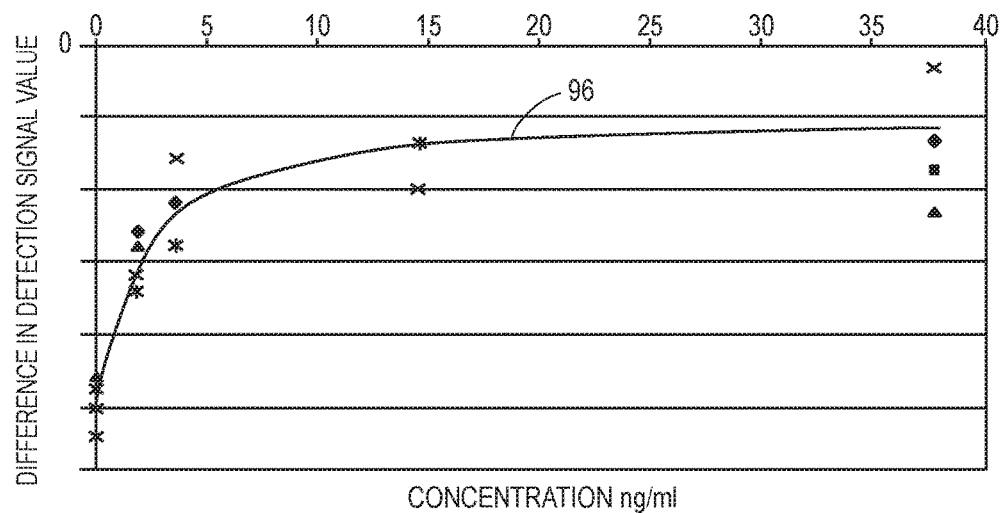
FIG. 7 illustrates a plot, for various test substance concentrations, of a metric that can be derived from an assay of the type shown in FIG. 6.

FIG. 7 plots various values of the metric J–H for different known concentrations of target antigen. A curve 96, which has been fitted to the results, is shown. Such a curve can thereafter be employed to estimate the target antigen concentration in live test situations.

5.4 Further Analyte Detection Arrangements

Figure 8:
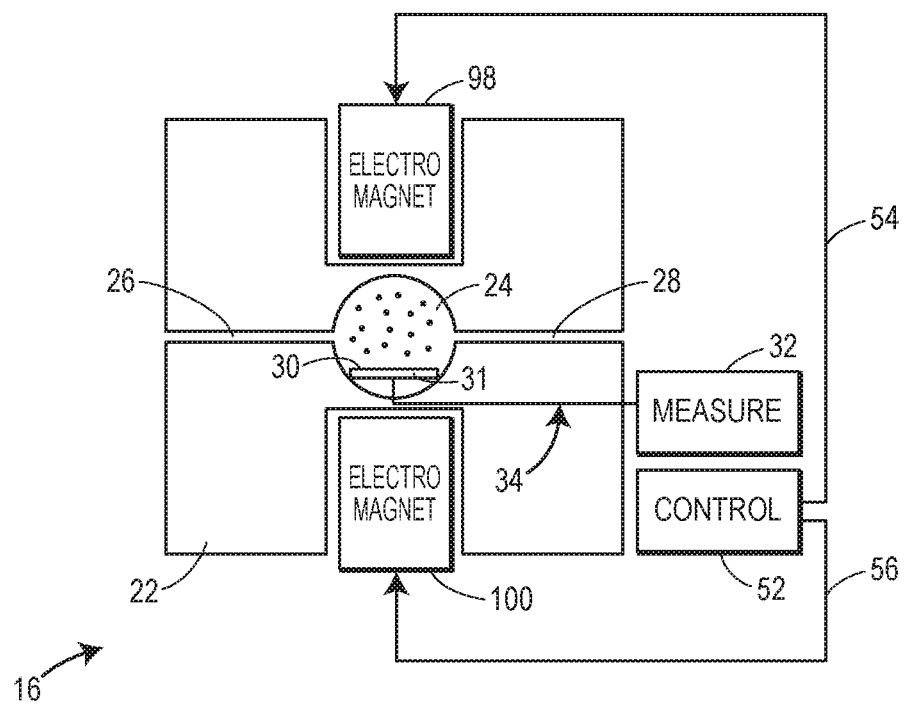
FIG. 8 illustrates a modified form of the test unit shown in FIG. 2.

Another embodiment of the invention is shown in FIG. 8. In this embodiment, the permanent magnets 40 and 46 have been replaced with electromagnets 98 and 100, the energisation of which is controlled by the control unit 52 in order to vary the magnetic field within the measurement chamber 24, e.g. to change the magnetic field from the collection state to the capture state.

Figure 9:
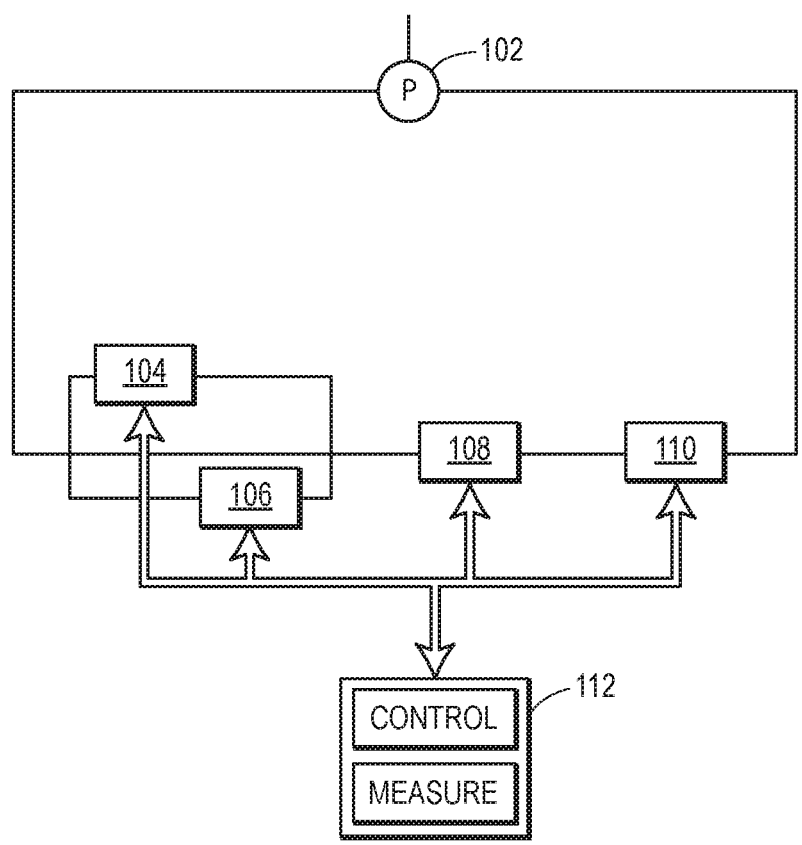
FIG. 9 illustrates a modified form of fluid analysis system containing several test stations.

FIG. 9 shows a further embodiment of the invention in which several sample chambers are used. Elements 104 to 110 each denote a test unit similar to test unit 16 of FIG. 1. However, in the embodiment of FIG. 9, the control and measurement functions associated with the plurality of sampling locations are collected into a single unit 112. This means, for example, that a single crystal oscillator can be used to provide a reference frequency for the VCOs associated with each of the sample chambers. Pump 102 takes in a volume of test liquid and circulates it through elements 104 to 110. It will be appreciated that elements 104 and 106 are placed in parallel whilst 108 and 110 are placed in series. The elements 104 to 110 need not all test for the same antigen. It is possible to utilise a temperature control system to keep multiple measurement chambers at the same temperature, should this be necessary given the types of test performed in those chambers (e.g. the temperature could be held the same within a group of chambers testing for the same antigen using the same antibody). A temperature control system can also be used to stabilize the temperature of those electronic components whose electrical properties or performance are temperature dependent (for example, components such as coil 68).

In the foregoing embodiments, a charge of the fluid under test is recirculated through the measurement chamber (or, as the case may be, chambers), and this is useful when attempting to detect a very low concentration of the target antigen. In other embodiments, however, it is possible to arrange that a given charge of test fluid is passed through a given measurement chamber just once. Additionally or alternatively, it is possible to hold a charge of test fluid with a given measurement chamber for a protracted period before perhaps processing another charge.

In the foregoing embodiments, antibody coated particles with attached antigen adhere to an antibody coating on a plate. Over time, it is possible that all of the magnetic particles will become adhered, or that no more particles can become adhered, resulting in the exhaustion of the measurement chamber. The measurement system can be configured to detect this condition (by monitoring the behaviour of the VCO that incorporates the coil that is associated with plate in question) and issue an appropriate indication to a user, who can take action to replenish the system. An embodiment in which replenishment is facilitated shall now be described.

Figure 10:
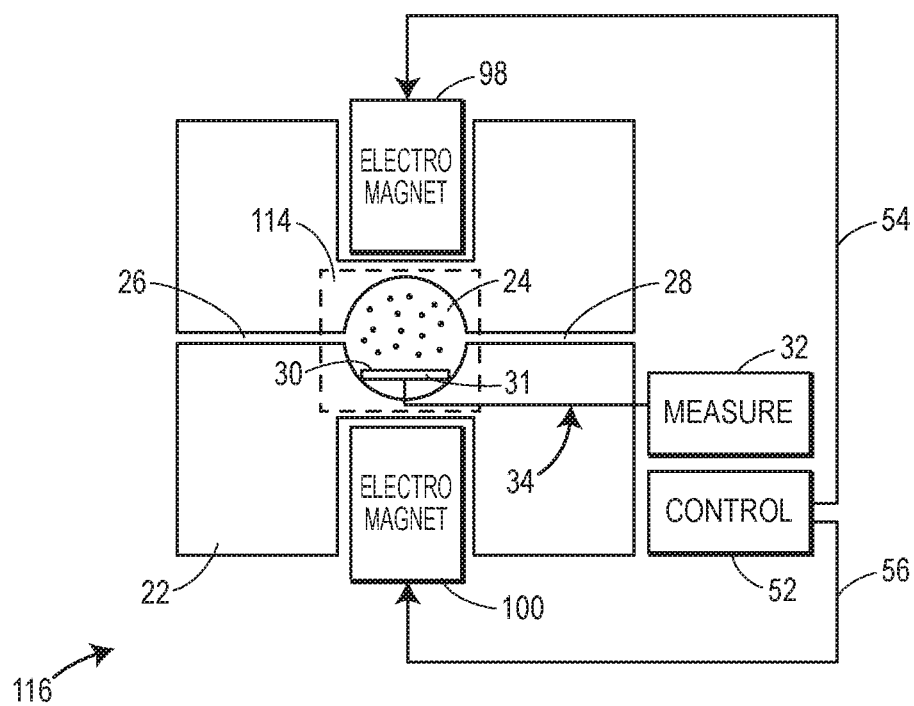
FIG. 10 illustrates a modified form of the test unit of FIG. 8 in which the measurement chamber is formed as a removable unit.

FIG. 10 illustrates a variant 116 of the test unit of FIG. 8 in which the measurement chamber is formed as a removable unit 114. In FIG. 10, elements carried over from FIG. 8 retain the same reference numeral and shall not be described in detail again. Of course, the concept of rendering the measurement chamber replaceable is not limited to the particular type of test unit shown in FIG. 8 and could be applied to any type of test unit, within reason.

In test unit 116, there is a removable cell 114 in block 22. This cell contains the measurement chamber 24, and the paramagnetic particles and plate 31 within it, and also parts of connection 34, bore 26 and bore 28. The cell 114 and the block 22 are provided with appropriate electrical connectors at the interface between the cell and the block in order to complete connection 34 when the cell is installed in the block. Likewise, fluid-tight connectors are provided at that interface to complete bores 26 and 28 when the cell 112 is installed in the block 22. Thus, an incumbent cell 114 can be replaced at will, e.g. with a fresh cell of the same type (when it is desired to refresh an exhausted measurement chamber) or with a cell of a different type in which the paramagnetic particles and the plate 31 are coated differently (in order to switch to testing for a different antigen). During fabrication of such a cell, the paramagnetic particles and the plate are given coatings appropriate for the antigen that the cell is to detect. The paramagnetic particles can be dried into the measurement chamber of the cell with suitable stabilising agents to allow rapid dispersal of individual particles when they are rehydrated by test fluid entering the chamber. Examples of suitable stabilising agents include sucrose, trehalose, and other poly-ionic compounds.

Figure 11:
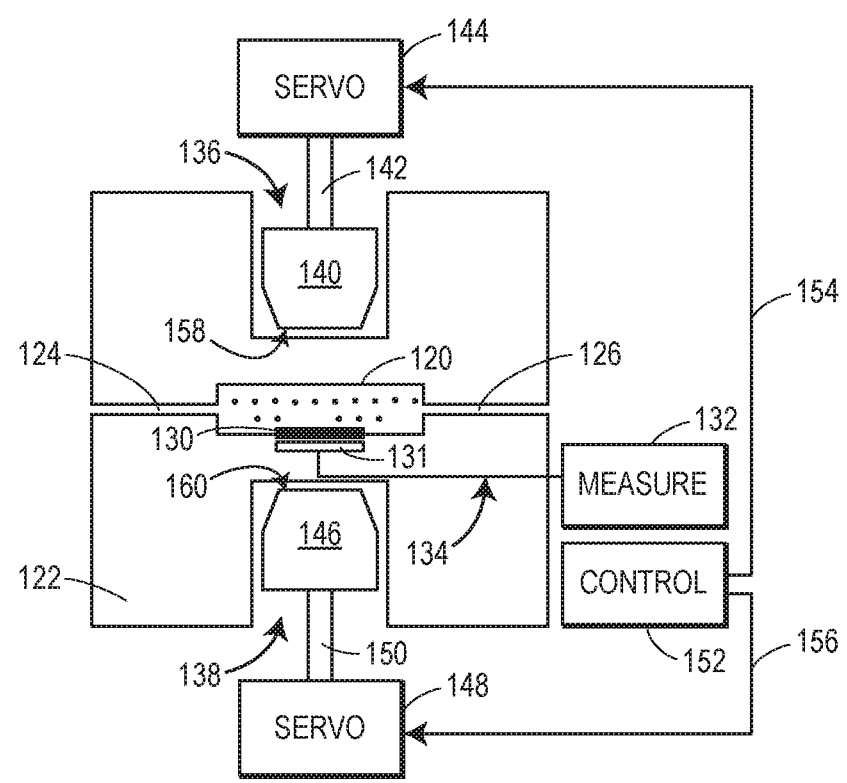
FIG. 11 illustrates schematically an alternative embodiment of a test unit.

FIG. 11 shows an alternative embodiment of a test unit of the system shown in FIG. 1. In this embodiment, the measurement chamber 120 is generally cylindrical, which helps to cause a controlled flow of fluid through the measurement chamber 120 and to reduce turbulence. The measurement chamber 120 is formed in the centre of a block 122 of a plastics material. Two bores 124, 126 are formed in the block 122 to connect the interior of the measurement chamber 120 with the exterior of the block 122, and the bores 124, 126 are tapered to assist in causing a controlled flow of fluid through the measurement chamber 126 and to reduce turbulence in the fluid. The mouth that bore 124 presents to the exterior of the block 122 is connected to tube 18 and the mouth that bore 126 presents to the exterior of the block is connected to tube 20. In this way, pump 12 can pass the test liquid through the measurement chamber 120. The measurement chamber 120 is populated with particles of paramagnetic material, which are denoted in FIG. 11 by the small circles lying within the measurement chamber 120. The paramagnetic particles are treated with a coating of a particular antibody to which the target antigen will bind.

A plate 128 is mounted in the bottom of the measurement chamber 120. The plate 128 has upper and lower major surfaces facing towards and away from the centre of the measurement chamber 120 respectively. The upper major surface of the plate 128 is covered with a coating 130 of the same antibody that has been applied to the paramagnetic particles. Disposed beneath the plate 128, externally of the measurement chamber 120, is an electrical coil 131 which is connected to a measurement unit 132 by means of an electrical connection 134.

Two cavities 136, 138 are provided in the upper and lower surfaces of the block 122. A permanent magnet 140 is slidably mounted within cavity 136. A shaft 138 connects permanent magnet 140 to a servo 144. The servo 144 is configured to act on the shaft 142 to vary the position of the magnet 140 within the cavity 136. That is to say, the servo 144 can raise and lower the magnet 140 in the cavity 136 so as to vary the distance of the magnet 140 from the measurement chamber 120. Analogously, a permanent magnet 146 is slidably mounted in cavity 138 and can be moved by a servo 148 by means of a shaft 150. The positions of the magnets 140, 146 within the cavities 136, 138 are governed by a control unit 152 that applies control signals to the servos 144, 148 through connections 154, 156. Surface 158 constitutes the north pole of the magnet 140 and surface 160 constitutes the south pole of the magnet 146. The magnets 140, 146 are closely fitted to their corresponding cavities 136, 138 so that the pole faces 158 and 160 and the major surfaces of the plate 128 remain parallel with one another as the magnets 140, 146 are moved.

As is the case for the test unit shown in FIG. 1, in the embodiment shown in FIG. 11 the positions of the magnets 140, 146 relative to the centre of the measurement chamber 120 dictate the magnetic field that is experienced by the paramagnetic particles that are located within the measurement chamber 120. The magnets 140, 146 may be positioned so as to cause the paramagnetic particles to adopt a sieve-like configuration by forming into strands that extend across the flow within the measurement chamber 120.

The electrical coil 131 in this embodiment is positioned outside of the measurement chamber 120, but performs the same role as the electrical coil of the embodiment of FIG. 2 in detecting the number of paramagnetic particles that are bound to antibody coating 130 of the plate 128.

Figure 12:
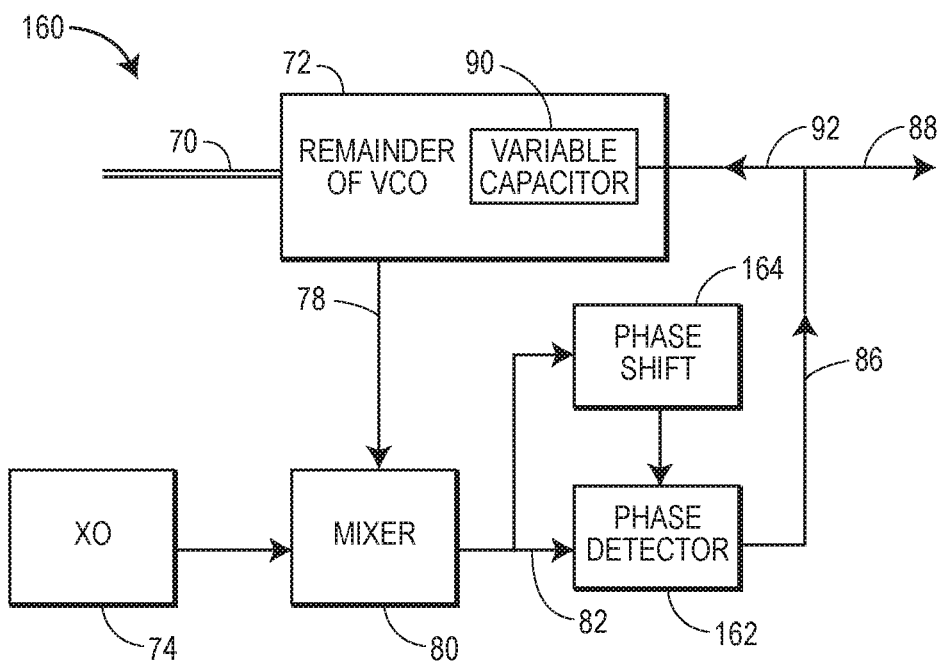
FIG. 12 illustrates schematically the main elements of an alternative measurement unit which is used in the test unit that is shown in FIG. 11

The system of FIG. 11 uses a detection unit, which is shown schematically in FIG. 12. The detection unit 160 is similar to the detection unit shown in FIG. 5, and thus like elements have the same reference numerals in FIG. 12. However, in the detection unit 160, the variable oscillator 81 is not present. Instead, the phase detector 162 and a phase shift unit 164 form a quadrature phase detector. In this arrangement the signal 82 is split into two components. One passes directly into one port of the phase detector 162 and the second is phase shifted by 90 degrees (at 70 KHz) and tuned by an appropriate capacitor-inductance-resistor band-pass filter in phase shift unit 164, before passing into the second port of the phase detector 162.

In this arrangement, the phase shift of the phase shift unit 164 is frequency dependent. Therefore, if the signal deviates from 70 KHz then the phase shift will deviate from the basic value (i.e. the value of the phase shift at 70 KHz). For example, frequencies greater than 70 KHz could result in a phase shift greater than 90 degrees and frequencies less than 70 KHz could result in a phase shift of less than 90 degrees. The output signal 86 from the phase detector 162 is proportional to the phase difference between the two signal components and hence the level of deviation of the signal 82 from 70 KHz. The phase detector output signal 86 adjusts the variable capacitor to bring the frequency of the VCO back to a frequency of 70 KHz away from the output signal of the crystal oscillator 74.

It will be noted, from FIG. 6 for example, that when measurements are taken as the paramagnetic particles are drawn to the plate 31/128 by the action of the magnetic filed generated by the magnets 40/46 and 140/146 that there is a step change in output voltage or frequency. This effect is caused by the proximity of the magnet 46/146, which is typically of Neodymium, to the electrical coil 68/131, which causes the inductance of the coil 68/131 to drop as the coil 68/131 approaches magnetic saturation. This has the effect of reducing the inductance of the coil 68/131, which tries to skew the frequency of signal 78.

The paramagnetic particles, which are typically of Magnetite or Ferrite, have the effect of increasing the permeability of the electrical coil 68/131, when in close proximity to the coil. This effectively increases the inductance of the electrical coil 68/131 and tends to try to lower the frequency of signal 78. Ferrite ceramics have the same effect on signal 78.

Thus, if the magnets 40/140 and 46/146 are given a tip made from Ferrite, or are coated with Ferrite, then the shift in the resonant frequency of the PLL/FLL circuit can be balanced out to a large extent. This results in good sensitivity to paramagnetic particles regardless of whether they are close to the electrical coil 68/131 or not.

Although the pole faces 58/160 and 60/160 are shown in FIGS. 2 and 11 as being flat, they may have a rounded profile to give an evenly distributed magnetic field at the flat surface of the plate 31/128, thus allowing an even layer of paramagnetic particles to form.

Although the example given above describes the use of the apparatus of the invention in performing sandwich assays, it will be appreciated by those skilled in the art that it can be used in performing other types of assays. For example, the apparatus could be used to perform a "displacement assay", in which antigen coated paramagnetic particles are initially bound to the on the upper surface of the plate 31 and are displaced, on the introduction of a sample containing the target antigen into the measurement chamber 24, from the plate 31 due to competitive interaction between the target antigen and the antigen of the paramagnetic particles, resulting in a change in the detection signal.

Alternatively, the apparatus of the invention can be used to perform a "competitive assay", in which a binding agent is attached to the upper surface of the plate 31. A first complementary binding agent, the target antigen, is introduced into the measurement chamber 24 with the sample, whilst a second complementary binding agent is attached to paramagnetic particles, and the first and second complementary binding agents compete to bind to the binding agent of the plate 31. The greater the concentration of the target antigen, the fewer paramagnetic particles will bind to the binding agent of the plate 31, and the detection signal will change accordingly.

5.5 Lysing Arrangement

Figure 13:
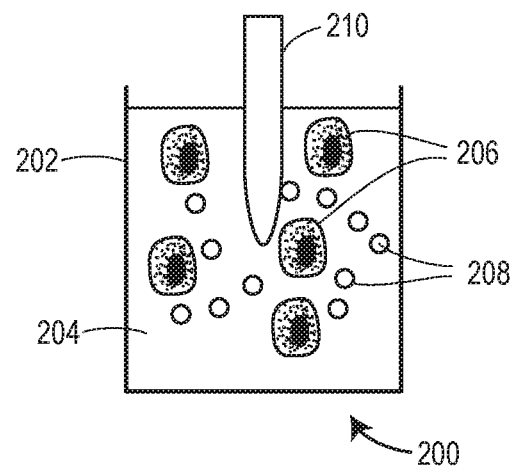
FIG. 13 illustrates an apparatus for cell lysis.

Referring now to FIG. 13, an apparatus for cell lysis is shown generally at 200, and comprises a lysing chamber 202 for holding a liquid 204 containing cells 206 to be lysed. The lysing chamber 202 also contains a plurality of particles 208 to enhance lysing. One or more sonicator probes 210 are provided to introduce energy in the form of sound waves at ultrasound frequencies into the chamber 202. Alternatively, one or more ultrasonic transducers may be integrated into the chamber 202 or positioned adjacent the chamber 122 to introduce the ultrasound energy into the chamber 202. Using particles of a suitable size and at a suitable density, ultrasound energy introduced into the chamber 202 by the sonicator probe 210 enables the particles 208 to acquire sufficient kinetic energy to lyse cells 206 mixed with the particles 208 in the chamber 202. The sonicator probe 210 may be activated in a continuous or pulsed fashion for a sufficient time to cause lysing of the cells 206 to occur.

Varying degrees of cell lysis can be achieved by adjusting one or more of the following parameters: the amount of ultrasound energy imparted, the type of particle 208 used, the concentration of the particles 208 or the size of the particles 208 used. The particles 208 should be of a size suitable to cause effective lysing. Preferably the particles 208 that are used to enhance the cell lysis are in the range of 0.1 µm-100 µm, or more preferably between 1 µm-20 µm. The particles 208 should be used in a concentration range suitable to cause effective lysing of the amount of cells 206 in the chamber 202.

The particles 208 should be appropriately constructed and/or formed from material of appropriate density to cause cell lysis. For example, the particles 208 may be made from metal or a plastics material, or a combination of metal and a plastics material, or may be of any other suitable material.

By controlling the degree of cell lysis, various cell components, for example proteins and organelles, can be released from the cells 206. Alternatively, the cells 206 can be greatly disrupted to release enhanced levels of intracellular protein above and beyond that released using sonication alone.

Any type of cell, including mammalian cells, non-mammalian cells, plant cells, bacteria, yeasts and spores or a mixture thereof, may be disrupted using the apparatus and method described above with reference to FIG. 13.

The apparatus shown in FIG. 13 may be used to identify, quantify or separate a component of interest from lysed cells. In this application, the particles 208 are coated with a binding agent to which intracellular components may bind, so as to capture such intracellular components. The binding agent may be, for example, an antibody, a lectin, DNA, RNA, a receptor protein or any other binding agent or moiety. The intracellular component of interest may be, for example, a protein or a cell-organelle that binds specifically to the binding agent. The intracellular component that binds to the binding agent may be identified, quantified or separated by using a label or reporter molecule which is associated with the intracellular component/binding agent complex formed during binding. For example, the label may be an enzyme which reacts with a suitable substrate to produce a coloured or fluorescent product. This reaction product may be used to identify, quantify or separate the intracellular component, as will be apparent to those skilled in the art.

Figure 14:
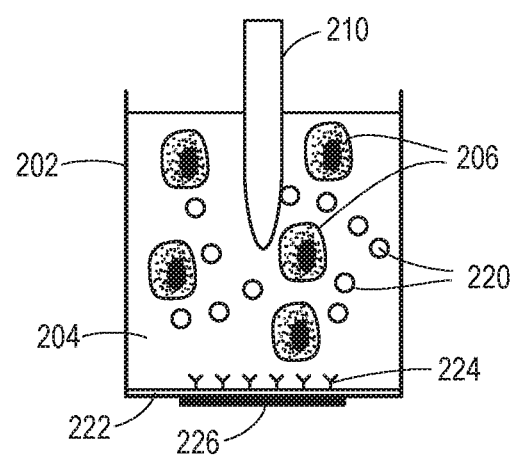
FIG. 14 illustrates a modified apparatus for cell lysis.

FIG. 14 shows a modified version of the cell lysis apparatus of FIG. 12 in which means for magnetically detecting a target component of a cell, such as a protein or cell-organelle, is provided. Elements common to this embodiment and the embodiment of FIG. 12 are denoted by like reference numerals. The lysing chamber 202 of this embodiment may form the measurement chamber of a fluid analysis system as described above with reference to FIGS. 1 to 11.

In this modified apparatus, the chamber 202 contains liquid 204 comprising a sample of cells 206 to be lysed, and a plurality of magnetic particles 220. The magnetic particles may be, for example, ferromagnetic, diamagnetic, paramagnetic or super-paramagnetic. The magnetic particles 220 are coated with a binding agent to which a target component, such as a protein or cell organelle, may bind. A sensor surface 222 is coated with a similar binding agent 224 to that used to coat the magnetic particles 220, such that the target component may bind to the binding agent on the sensor surface 222. A magnetic sensing means 226 is provided beneath the sensor surface. The magnetic sensing means 226 may be integrated into the lysis chamber 202, or may be positioned adjacent the lysis chamber 202. The magnetic sensing means 226 may be a magnetic coil or may be a resonant coil magnetometer, a magneto-resistive sensor, a micro-machined cantilever device or a superconducting quantum interference device, for example.

In use of the apparatus of FIG. 14, liquid containing the cells 206 to be lysed is placed in the chamber 202 with the magnetic particles 220 and a sonicator probe 210 is activated either continuously or in a pulsed manner for a time sufficient for lysis of the cells 206 to occur.

Figure 15:
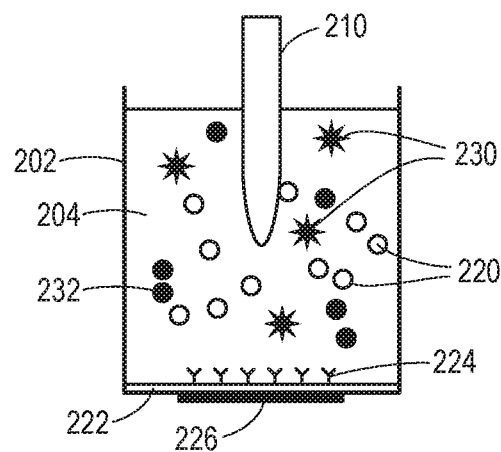
FIG. 15 shows the apparatus of FIG. 14 after lysis has occurred.

FIG. 15 shows the apparatus of FIG. 14 after lysis has occurred. Elements common to this Figure and FIGS. 13 and 14 are denoted by like reference numerals.

Lysing of the cells 206 by continuous or pulsed activation of the sonicator probe 210 produces lysed cells 230 and causes the target components such as protein(s) and/or cell organelle(s) to bind to the binding agent that is used to coat the magnetic particles 220, to form a bound complex comprising the component (e.g. protein(s) or cell organelle(s)) of interest and magnetic particles, hereinafter referred to as "bound particles" 232.

Figure 16:
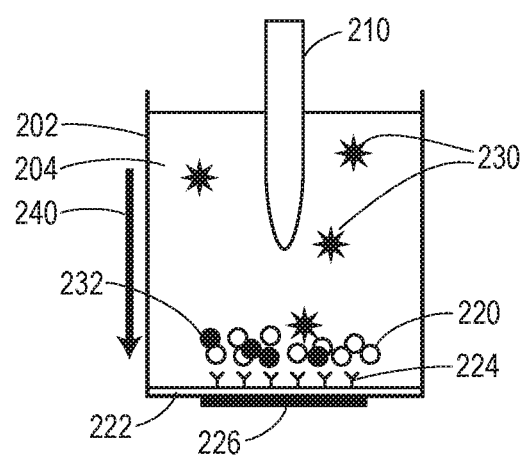
FIG. 16 shows the apparatus of FIGS. 14 and 15 with an external magnetic field applied in a first direction.

FIG. 16 shows the apparatus of FIGS. 14 and 15 when an external magnetic force is used to manipulate the magnetic particles 220 after lysis has taken place. Again, common elements are denoted by like reference numerals. The external magnetic force may be provided by one or more permanent magnets, or by adjusting one or more electromagnets, for example. The magnets may be mounted externally of the chamber 202 or may be integrated into the chamber 202.

The externally applied magnetic force acts in the direction of the arrow 240 and is used to pull the bound particles 232 and the magnetic particles 220 towards the sensor surface 222, where the bound particles 232 bind to the binding agent 224 on the sensor surface 222. The bound particles 232 become cross-linked to the sensor surface 222, causing them to be immobilised on the sensor surface 222.

Figure 17:
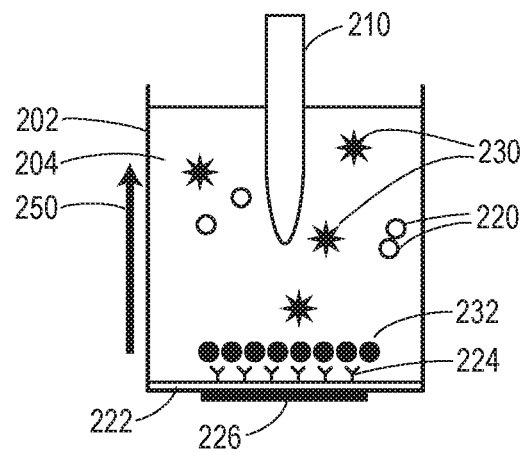
FIG. 17 shows the apparatus of FIG. 14 when the direction of the magnetic field is subsequently reversed.

FIG. 17 shows the apparatus of FIG. 16 with the external magnetic force applied in the direction of the arrow 250 (i.e. the direction of the external magnetic field is reversed), and used to pull unbound magnetic particles 220 away from the sensor surface 222, thus leaving just the bound particles 232 attached to the binding agent 224 on the sensor surface 222, which allows the sensing means 226 to quantify the amount of bound particles 232 present. The amount of bound particles 232 detected by the sensing means 226 can then be used to determine the amount of the target components such as protein(s) and/or cell organelle(s) present.

Using the method and apparatus described above with reference to FIGS. 14 to 17, lysis of cells and identification, quantification or separation of intracellular components such as proteins and cell-organelles to be performed in the same vessel.

Experiments carried out in relation to lysis of cells using particles will now be described.

5.6 Further Results

Figure 18:
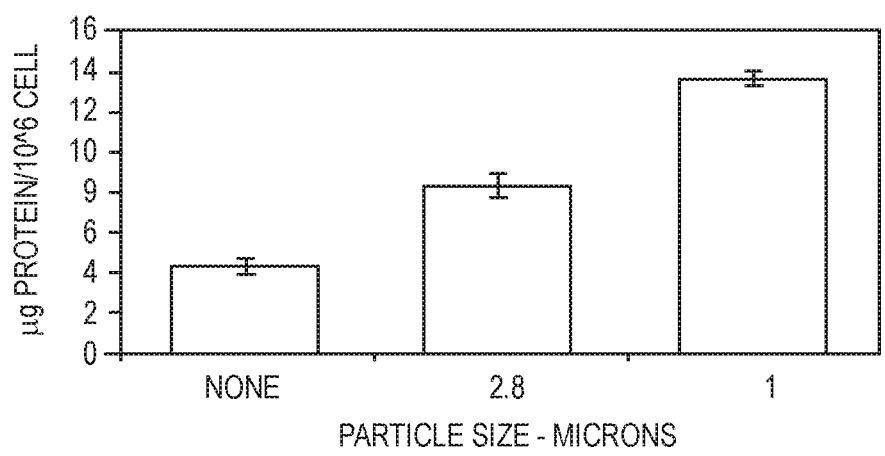
FIG. 18 shows experimental results for the amount of total protein released after lysis of Jurkat cells in the apparatus of FIGS. 12-15 when no particles are present, when particles of 2.8 µm diameter particle are present and when particles of 1 µm are present.

FIG. 18 plots the amount of total protein released after sonication of Jurkat cells in the lysis chamber when no particles are present, when particles of 2.8 µm diameter are present and when particles of 1 µm diameter are present.

Figure 19:
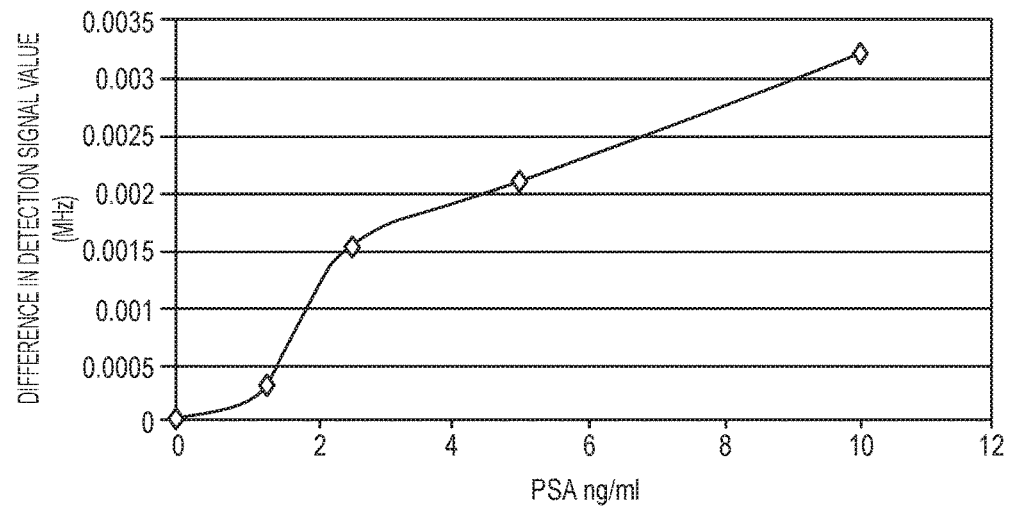
FIG. 19 shows a plot of the dose response of a magnetoimmunoassay to prostatic specific antigen (PSA) released from LNCAP cells by particle enhanced sonication using the apparatus of FIGS. 13-16.

FIG. 19 shows a plot of the dose response of a magneto-immunoassay to prostatic specific antigen (PSA) released from LNCAP cells by particle enhanced sonication.

Figure 20:
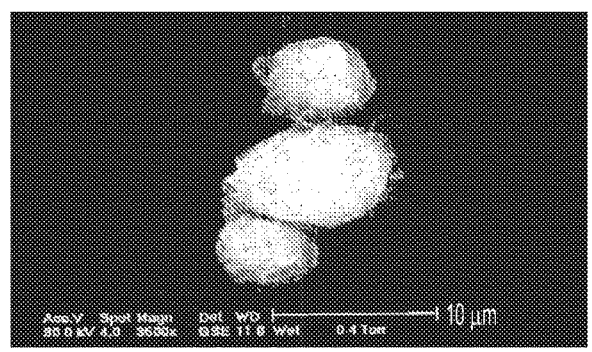
FIG. 20 shows a Scanning Electron Microscope (SEM) image of Jurkat cells sonicated with no paramagnetic particles present, using the apparatus shown in FIG. 11.

FIG. 20 shows a Scanning Electron Microscope (SEM) image of Jurkat cells sonicated with no paramagnetic particles present.

Figure 21:
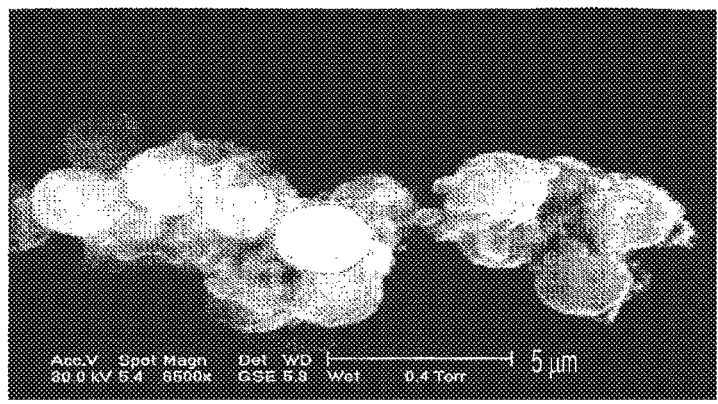
FIG. 21 shows a SEM photo of Jurkat cells sonicated in the presence of 2.8 µm particles.

FIG. 21 shows a SEM photo of Jurkat cells sonicated in the presence of 2.8 µm particles.

Figure 22:
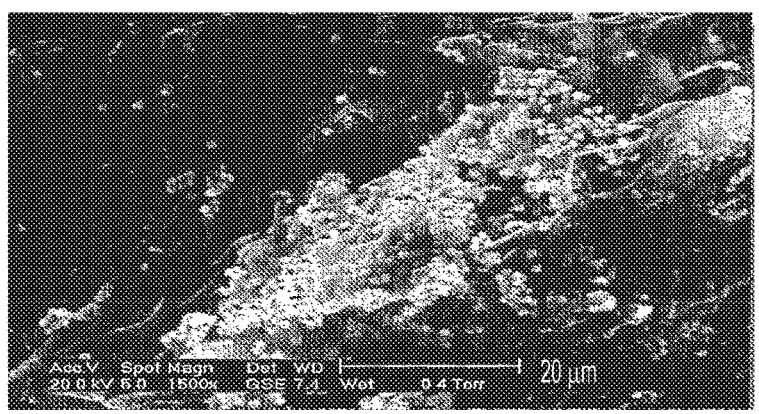
FIG. 22 shows a SEM photo of Jurkat cells sonicated in the presence of 1 µm particles.

FIG. 22 shows a SEM photo of Jurkat cells sonicated in the presence of 1 µm particles.

In a specific example using the apparatus shown in FIG. 13, Jurkat cells were lysed using different sized particles in conjunction with ultrasound.

Jurkat cells were cultured in 75 mm² tissue culture flasks in sterile penicillin/streptomycin supplemented RPMI-1640 containing 10% newborn calf serum and L-glutamine and incubated in a humidified atmosphere at 37.5° C. with $CO_2$. The cells were routinely passaged 1:4 (1 part cells: 4 parts growth medium) every 2 to 3 days. At 3 days post-passage, the cells were centrifuged for 5 minutes at 21° C. at 1500 rpm. The cells were then re-suspended in 1 ml penicillin/streptomycin-supplemented RMPI (50 ml of FBS+5 ml L-Glutamine+5 ml Penicillin & Streptomycin to 500 ml of RPMI 1640). The cells were counted by the Trypan Blue exclusion method, in which a 20 µl sample of the cell suspension was mixed with 20 µl Trypan Blue stain (0.2% w/v Trypan blue dissolved in PBS and stored at 4° C.). The suspension was gently vortexed and 10 µl of the stained cells were counted using a haemocytometer.

To demonstrate the effect of particle size on the efficiency of cell lysis Jurkat cells were centrifuged at 200 g for 10 minutes and the supernatant was discarded. The pellets obtained were re-suspended in 1 ml phosphate buffer saline in the chamber, and 5 µl of 2.8 µm or 1 µm paramagnetic particles (Dynabeads) were added. The mixture was then treated with a sonicator probe for 1 minute. To prevent excessive heat generated by the probe, the sample was immersed in an ice bath and the ultrasound was applied in multiple short bursts. The effect of the sonication with and without particles was quantified by measuring total protein released into the supernatant and the physical effect on the cells was studied using SEM (Scanning Electron Microscopy).

The addition of paramagnetic particles to the cells prior to sonication enhanced the amount of protein released from the cells in a given time. Moreover, paramagnetic particles of different sizes enhanced the protein released from the cells to different extents. Without paramagnetic particles the sonication process released 4 µg protein/$10^6$ cells, with the addition of 2.8 µm particles (Dynabeads), twice as much protein was released from the cells (8 µg/$10^6$) and 1.0 µm particles (Dynabeads) released approximately three and half times as much protein (14 µg/$10^6$), as is shown in FIG. 16. A significant difference was observed in the concentration of protein released by the sonication probe alone and combined with paramagnetic particles as shown by the total protein measurement ($P<0.001$).

Scanning Electron Microscopy (SEM) was used to evaluate the effect of sonication on cell morphology with and without the paramagnetic particles (see FIGS. 18, 19 and 20). Surprisingly, the different size of particles had a very different effect on the cells. 2.8 µm particles appeared to cause coagulation of the intracellular proteins whereas 1.0 µm particles induced the formation of membranous like structures.

In a second example, the apparatus shown in FIGS. 14-17 was used to demonstrate the magnetic detection of intracellular prostatic specific antigen. In this case LNCAP cells were lysed in the presence of 1 µm paramagnetic particles which were previously coated with anti-PSA. The floor of the lysis chamber incorporated the magnetic sensor which had a second anti-PSA antibody immobilised on its surface. Following sonication in the presence of the paramagnetic particles, an external magnetic field was applied to all the paramagnetic particles down to the sensor surface. Particles which had PSA bound to the surface by the antibody interaction were cross-linked to the sensor surface by the binding of the second antibody immobilised on the sensor surface to the captured PSA molecule on the paramagnetic particle. The captured PSA acted as a biological bridge holding the particle on the surface through the immunological linkage. A second external magnetic field was applied to remove unbound paramagnetic particles prior to measurement. A resonant coil magnetometer, lying underneath the sensor surface, was used to detect the presence of paramagnetic particles attached to the sensor surface. FIG. 18 shows the dose response of a magneto-immunoassay for PSA released from LNCAP cells by particle enhance lysis.

These examples demonstrate that paramagnetic particles used in magneto-biosensors can be used to enhance the release of intracellular proteins from the cells, as part of an integrated measuring system for the rapid measurement of intracellular proteins.

The invention claimed is:

1. Fluid testing apparatus comprising:
   a measurement chamber having a binding site to which can attach magnetic particles which have become associated with a target substance in the fluid;
   an oscillator circuit comprising an inductance and a variable capacitance in resonant combination to set the frequency of the circuit's output signal;
   a detector configured to generate a signal for altering the variable capacitance, wherein the inductance is influenced by the quantity of magnetic particles at the binding site and the detector is configured to generate a signal to alter the variable capacitance to maintain the frequency of the circuit's output in the face of changes in the quantity of magnetic particles at the binding site;
   a magnet that is enclosed within a first cavity of the fluid testing apparatus and slidably mounted within the first cavity so as to follow a predetermined path which maintains a pole face of the magnet substantially parallel to a binding surface of the measurement chamber such that magnetic particles orientate themselves in a manner that allows them to move towards the binding surface; and
   a control unit configured to issue control signals to move the magnet from a first position to a second position, wherein when the magnet is in the first position the fluid testing apparatus is operable in a first state in which the magnetic particles interact with the fluid such that magnetic particles become associated with the target substance in the fluid, and when the magnet is in the second position, the magnet is configured to generate a magnetic field within the measurement chamber to cause the apparatus to operate in a second state in which the magnetic particles are drawn to collect on the binding site, and wherein the control unit is configured to issue a control signal to move the magnet to the second position after a period of operation in the first state.

2. Fluid testing apparatus according to claim 1, further comprising a recorder configured to record the signal generated by the detector over time, configured to quantify the quantity of magnetic particles at the binding site on the basis of the signal generated by the detector.

3. Fluid testing apparatus according to claim 1 further comprising a second magnet that is enclosed within a second cavity of the fluid testing apparatus and slidably mounted within the second cavity so as to follow a predetermined path which maintains a pole face of the magnet substantially parallel to a binding surface of the measurement chamber such that magnetic particles orientate themselves in a manner that allows them to move towards the binding surface, wherein the control unit is operable to issue control signals to move the second magnet from a first position to a second position, wherein when the second magnet is in the first position the fluid testing apparatus is operable in the first state, and when the second magnet is in the second position, the apparatus operates in the second state, and wherein the control unit is operable to issue a control signal to move the second magnet to the second position after a period of operation in the first state.

4. Fluid testing apparatus according to claim 3 wherein the apparatus comprises a second servo which is operable to move the second magnet along the predetermined path.

5. Fluid testing apparatus according to claim 3 wherein when the apparatus operates in the first state the magnetic particles form strands that extend across the measurement chamber.

6. Fluid testing apparatus according to claim 1 wherein the apparatus comprises a servo which is operable to move the magnet along the predetermined path.

7. Fluid testing apparatus according to claim 1, wherein the detector comprises a phase detector for comparing the phase of the circuit's output signal with the phase of a reference signal.

8. Fluid testing apparatus according to claim 7, further comprising a mixer which mixes the circuit's output signal with a reference signal to frequency-downconvert the circuit's output signal prior to the action of the phase detector.

9. Fluid testing apparatus according to claim 1, wherein the particles are paramagnetic.

10. Fluid testing apparatus according to claim 1, wherein the particles have a coating to which the target substance attaches.

11. Fluid testing apparatus according to claim 1, wherein the binding site has a coating by which particles carrying the target substance are captured.

12. Fluid testing apparatus according to claim 1, wherein the detector is a quadrature phase detector.

13. A method of testing a fluid, the method comprising:
introducing a fluid to be tested into a measurement chamber of a fluid testing apparatus, wherein the measurement chamber has a binding site to which can attach magnetic particles which have become associated with a target substance in the fluid, wherein the fluid testing apparatus comprises:
an oscillator circuit comprising an inductance and a variable capacitance in resonant combination to set the frequency of the circuit's output signal; and
a detector configured to generate a voltage for altering the variable capacitance, wherein the inductance is influenced by the quantity of magnetic particles at the binding site and the detector is configured to generate a voltage to alter the variable capacitance to maintain the frequency of the circuit's output in the face of changes in the quantity of magnetic particles at the binding site, the fluid testing apparatus further comprising a magnet that is enclosed within a first cavity of the fluid testing apparatus and slidably mounted within the first cavity so as to follow a predetermined path which maintains a pole face of the magnet substantially parallel to a binding surface of the measurement chamber such that magnetic particles orientate themselves in a manner that allows them to move towards the binding surface and a control unit configured to issue control signals to move the magnet from a first position to a second position, wherein the method further comprises:

moving the magnet to the first position to cause the apparatus to operate in a first state in which the magnetic particles interact with the fluid such that magnetic particles become associated with the target substance in the fluid; and after a period of operation in the first state, moving the magnet to the second position to cause the apparatus to operate in a second state in which the magnetic particles are drawn to collect on the binding site.

14. A method according to claim 13, wherein the fluid testing apparatus further comprises a second magnet that is enclosed within a second cavity of the fluid testing apparatus and slidably mounted within the second cavity so as to follow a predetermined path which maintains a pole face of the magnet substantially parallel to a binding surface of the measurement chamber such that magnetic particles orientate themselves in a manner that allows them to move towards the binding surface and the control unit is operable to issue control signals to move the second magnet from a first position to a second position, wherein when the second magnet is in the first position the fluid testing apparatus is operable in the first state, and when the second magnet is in the second position, the apparatus operates in the second state, wherein the method further comprises:

moving the second magnet to the first position to cause the apparatus to operate in the first state; and after a period of operation in the first state, moving the second magnet to the second position to cause the apparatus to operate in the second state.

15. A method according to claim 13 wherein the fluid testing apparatus comprises a servo which is operable to move the magnet along the predetermined path.

16. A method according to claim 14 wherein the apparatus comprises a second servo which is operable to move the second magnet along the predetermined path.

17. A method according to claim 14 wherein when the apparatus operates in the first state the magnetic particles form strands that extend across the measurement chamber.

* * * * *